(12) United States Patent
Biyani

(10) Patent No.: US 8,900,248 B2
(45) Date of Patent: Dec. 2, 2014

(54) INSERTION ASSEMBLY FOR MINIMALLY INVASIVE SPINAL SURGERY

(75) Inventor: Ashok Biyani, Sylvania, OH (US)

(73) Assignee: The University of Toledo, Toledo, OH (US)

( * ) Notice: Subject to any disclaimer, the term of this patent is extended or adjusted under 35 U.S.C. 154(b) by 344 days.

(21) Appl. No.: 12/484,711

(22) Filed: Jun. 15, 2009

(65) Prior Publication Data

US 2010/0049206 A1    Feb. 25, 2010

Related U.S. Application Data

(60) Provisional application No. 61/061,568, filed on Jun. 13, 2008.

(51) Int. Cl.
| | |
|---|---|
| *A61B 17/58* | (2006.01) |
| *A61B 17/60* | (2006.01) |
| *A61F 2/00* | (2006.01) |
| *A61B 17/70* | (2006.01) |
| *A61B 17/16* | (2006.01) |

(52) U.S. Cl.
CPC .......... *A61B 17/7002* (2013.01); *A61B 17/708* (2013.01); *A61B 17/1604* (2013.01); *A61B 17/7085* (2013.01)
USPC ........................................... 606/104

(58) Field of Classification Search
CPC .......................... A61B 17/1757; A61B 17/708
USPC .............................................. 606/104
See application file for complete search history.

(56) References Cited

U.S. PATENT DOCUMENTS

| | | | | | |
|---|---|---|---|---|---|
| 5,531,751 | A | * | 7/1996 | Schultheiss et al. | 606/96 |
| 6,090,113 | A | * | 7/2000 | Le Couedic et al. | 606/914 |
| 7,455,685 | B2 | * | 11/2008 | Justis | 606/246 |
| 7,465,306 | B2 | * | 12/2008 | Pond et al. | 606/86 A |
| 7,563,264 | B2 | * | 7/2009 | Landry et al. | 606/86 A |
| 7,666,188 | B2 | * | 2/2010 | Anderson et al. | 606/104 |
| 7,666,189 | B2 | * | 2/2010 | Gerber et al. | 606/104 |
| 7,909,830 | B2 | * | 3/2011 | Frigg et al. | 606/86 A |
| 7,951,175 | B2 | * | 5/2011 | Chao et al. | 606/279 |
| 7,967,826 | B2 | * | 6/2011 | Colleran et al. | 606/99 |
| 8,034,084 | B2 | * | 10/2011 | Landry et al. | 606/265 |

(Continued)

OTHER PUBLICATIONS

DePuy Spine catalog, pp. 1-49 (admitted prior art), understood to be before Jun. 13, 2008.

(Continued)

*Primary Examiner* — David Bates
(74) *Attorney, Agent, or Firm* — MacMillan, Sobanski & Todd, LLC

(57) ABSTRACT

A telescopic insertion assembly is configured to insert a pedicle screw into a vertebral body. The insertion assembly includes an attachment fixture having one end configured to mate with the pedicle screw and another end having a ridged portion. A center tube is provided having one end slidably attached to the attachment fixture and another end having an internally ridged portion. A telescoping member has one ridged end configured to slidably attach to the center tube and another end having a yoke. The telescoping member is configured to extend the yoke to different distances from the center tube. An alignment member is configured to hingeably attach to the yoke of the telescoping member. The alignment member is configured to rotate from a first position to a second position. The second position of the alignment member is above a top surface of a patient's skin.

16 Claims, 15 Drawing Sheets

(56) References Cited

U.S. PATENT DOCUMENTS

| | | | |
|---|---|---|---|
| 8,512,343 B2 * | 8/2013 | Dziedzic et al. | 606/86 A |
| 8,512,383 B2 * | 8/2013 | Mclean | 606/279 |
| 8,672,944 B2 * | 3/2014 | Boachie-Adjei et al. | 606/86 A |
| 8,709,044 B2 * | 4/2014 | Chao et al. | 606/246 |
| 2005/0070917 A1 * | 3/2005 | Justis | 606/104 |
| 2005/0234449 A1 * | 10/2005 | Aferzon | 606/61 |
| 2005/0245928 A1 * | 11/2005 | Colleran et al. | 606/61 |
| 2006/0111713 A1 * | 5/2006 | Jackson | 606/61 |
| 2007/0078460 A1 * | 4/2007 | Frigg et al. | 606/61 |
| 2008/0077155 A1 * | 3/2008 | Diederich et al. | 606/105 |
| 2008/0262318 A1 | 10/2008 | Gorek et al. | |

OTHER PUBLICATIONS

Globus, Minmally Invasive Products, Globus Medical, p. 1 of 2 (admitted prior art), understood to be before Jun. 13, 2008.

\* cited by examiner

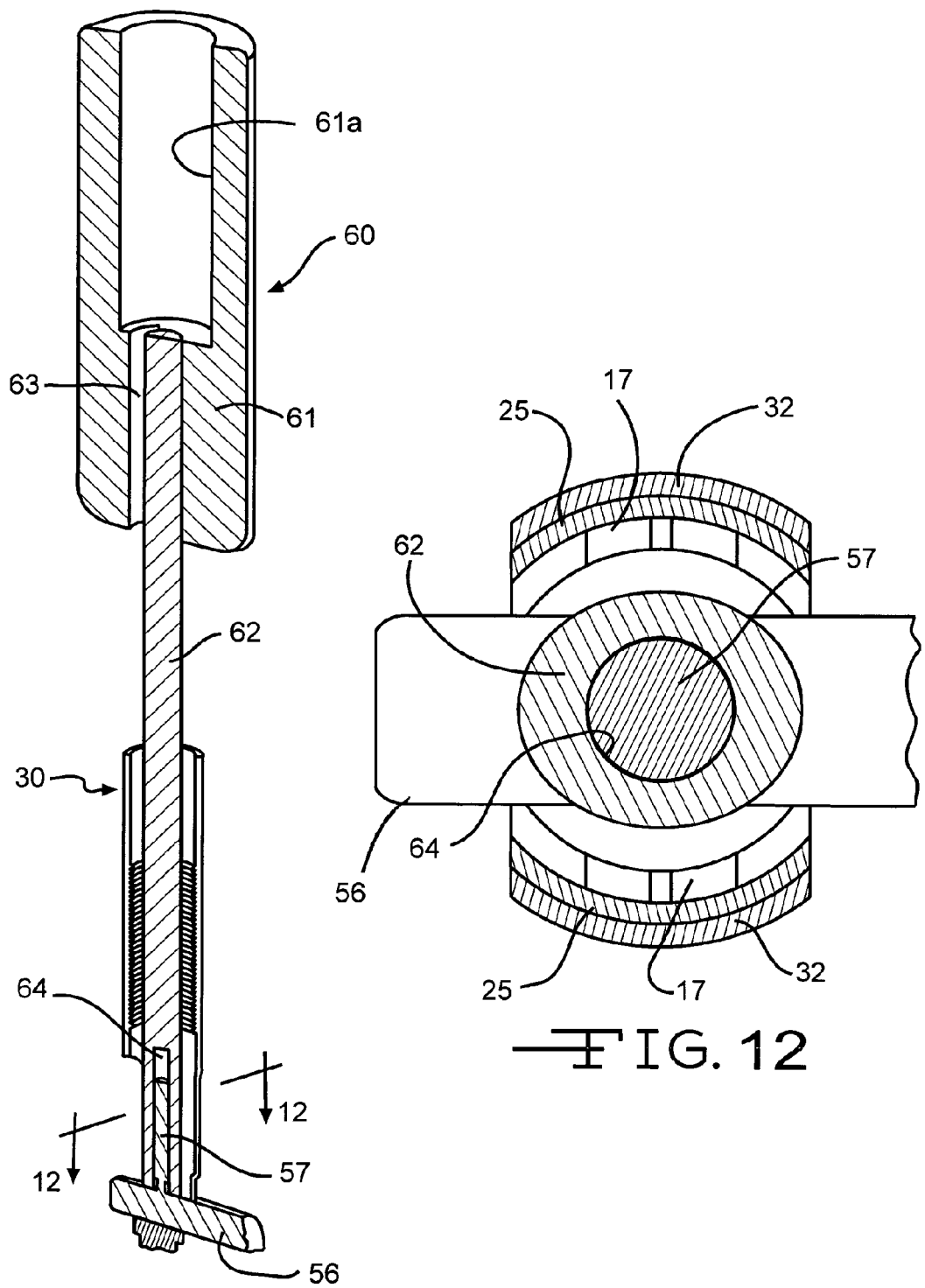

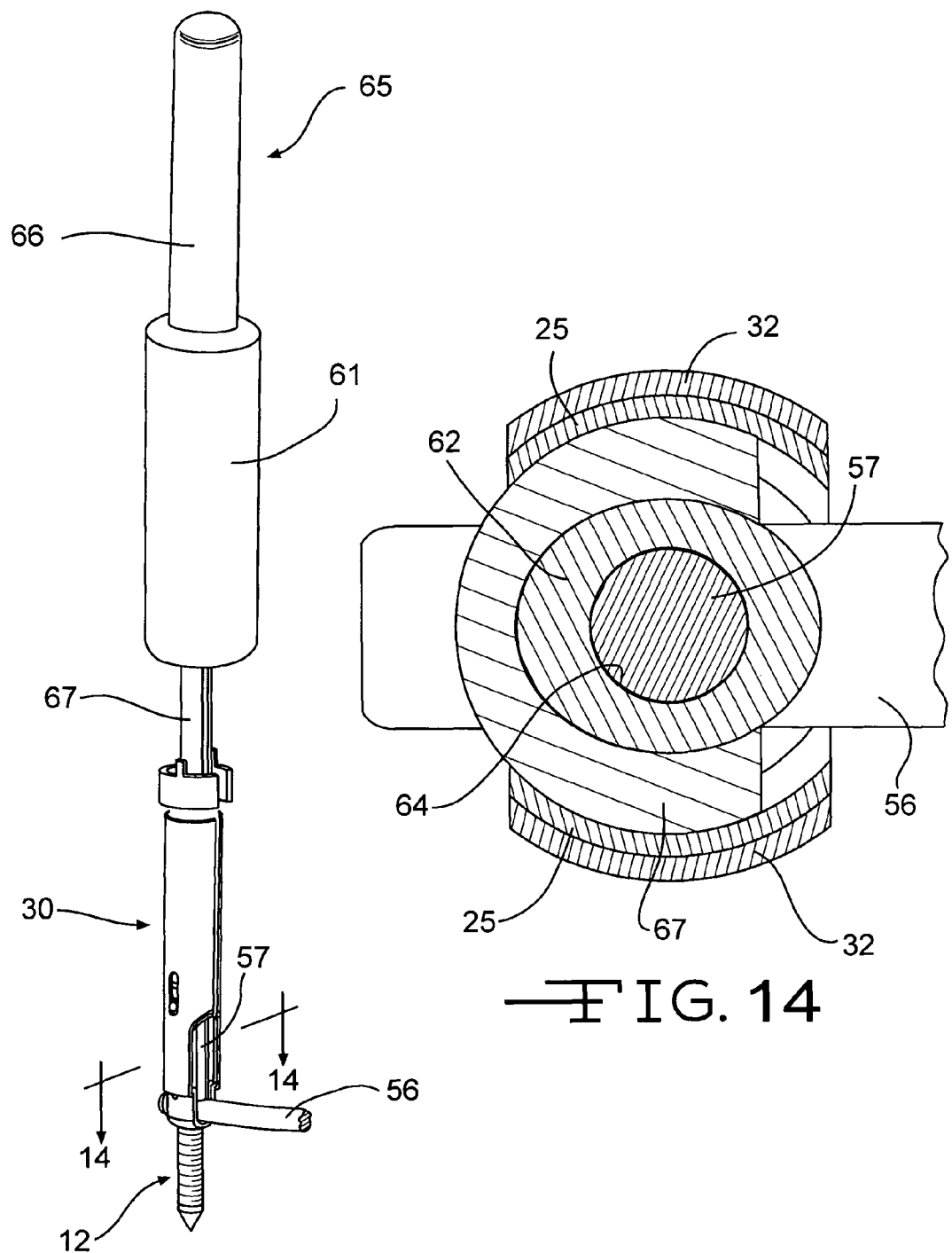

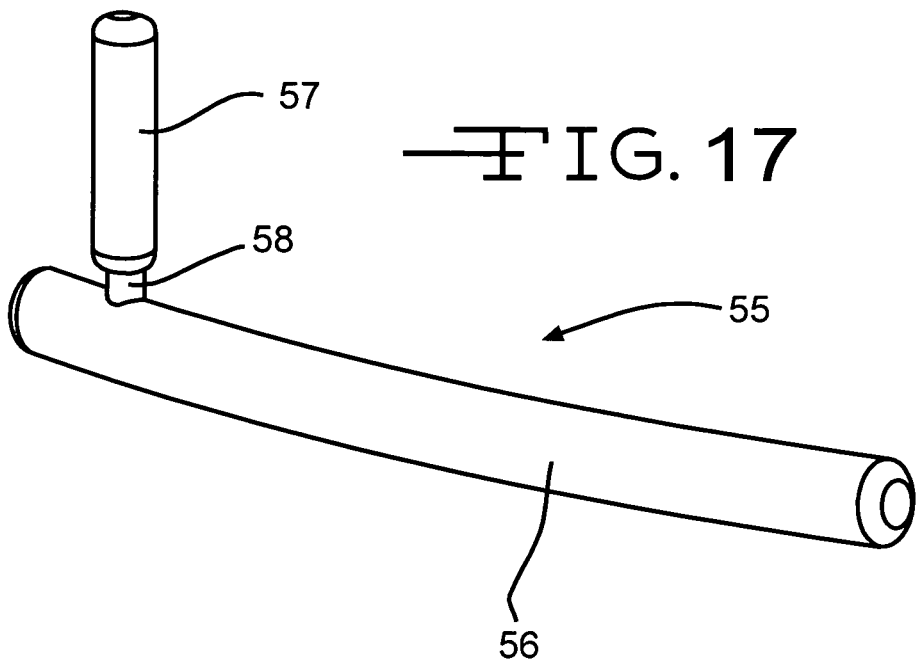
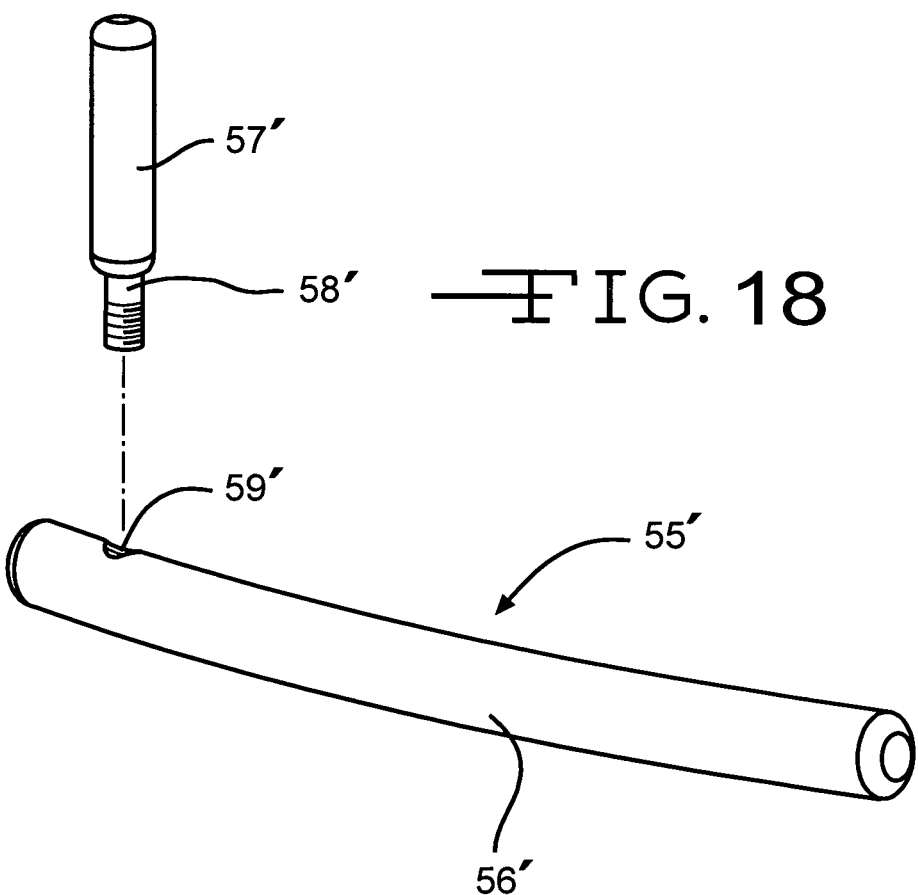

INSERTION ASSEMBLY FOR MINIMALLY INVASIVE SPINAL SURGERY

STATEMENTS REGARDING FEDERALLY SPONSORED RESEARCH OR DEVELOPMENT AND CROSS-RELATED APPLICATIONS

This invention was not made with any government support. This application claims the benefit of U.S. Provisional Application No. 61/061,568 filed Jun. 13, 2008, the disclosure of which is incorporated herein by reference.

BACKGROUND OF THE INVENTION

This invention relates to the field of orthopedic surgery and more particularly to the area of spinal surgery. Spinal surgery can involve the insertion of pedicle screws into adjacent vertebral bodies. Minimally invasive surgery involves the use of small incisions. The use of small incisions provides for reduced muscle damage, decreased blood loss, less postoperative pain, reduced scarring, shorter inpatient hospital stay, and improved operative results. During minimally invasive surgery, pedicle screws can be inserted through small incisions using imaging or navigational guidance. Small incisions in the patient's skin can be made precisely over the desired location, and pedicle screws can be inserted utilizing extended tube assemblies. Once all of the desired screws have been inserted, a longitudinal member, such as for example a rod, can be inserted in a percutaneous manner and secured to the pedicle screws with desired retainers.

However, it can be difficult to maneuver the extended screw assemblies in the event that multiple pedicle screws are being inserted. Additionally, lumbar lordosis can produce crowding in the surgical area, which can result in difficulty in aligning the extended tube assemblies. Thus, there is a need for an improved insertion assembly for placement of pedicle screws that overcomes aforementioned drawbacks of previously described insertion tube assemblies.

SUMMARY OF THE INVENTION

According to this invention, there is provided a telescopic insertion assembly configured to insert a pedicle screw into a vertebral body. The insertion assembly includes an attachment fixture having one end configured to mate with the pedicle screw and another end having a ridged portion. A center tube is provided having one end slidably attached to the attachment fixture and another end having an internally ridged portion. A telescoping member has one ridged end configured to slidably attach to the center tube and another end having a yoke. The telescoping member is configured to extend the yoke to different distances from the center tube. An alignment member is configured to hingeably attach to the yoke of the telescoping member. The alignment member is configured to rotate from a first position to a second position. The second position of the alignment member is above a top surface of a patient's skin.

According to this invention, there is also provided a telescopic insertion assembly configured to insert a pedicle screw into a vertebral body. The telescopic insertion assembly includes an attachment fixture having one end configured to mate with the pedicle screw and another end having a ridged portion. A center tube has one end slidably attached to the attachment fixture and another end having an internal portion. A telescoping member has one end slidably attached to the center tube and another end having a collar. The collar includes a plurality of apertures. The telescoping member is configured to extend the collar to different distances from the center tube. An alignment tool has a plurality of prongs configured to engage the plurality of apertures in the collar. The alignment tool maintains the collar of the telescoping member at a level above a top surface of a patient's skin.

According to this invention, there is also provided a reducing retainer configured for retaining a longitudinal member in a head of a pedicle screw. The reducing retainer includes a retainer portion configured to attach to the head of the pedicle screw and retain a longitudinal member in the head. An extension section is connected to the retainer portion. The extension section has a weakened area. A head portion is connected to the extension section and has a drive structure. Rotational movement applied to the drive structure is configured to seat the longitudinal member in the head of the pedicle screw. Further rotational movement of the drive structure is configured to break the weakened area of the extension section. The extension section and the drive structure can be removed after the weakened area is broken.

According to this invention, there is also provided an assembly configured for centralizing of a longitudinal member within a plurality of telescopic insertion assemblies. The assembly includes a rod holder having a handle and an extension member. The handle has an aperture. The extension member has an aperture. The aperture of the extension member is configured for placement over an extension of a longitudinal member. A centralizer has a handle and an elongated member. The elongated member is configured for insertion through the aperture in the handle of the rod holder. The elongated member is further configured to substantially encircle the extension member. The centralizer centralizes the longitudinal member among the plurality of telescopic insertion assemblies.

According to this invention, there is also provided a center tube for use in a telescopic insertion assembly. The center tube includes a lower end configured for releasable attachment to a pedicle screw, a middle portion connected to the lower end and an upper end connected to the middle portion. A pivotable section is pivotably attached to the middle portion and extends into the upper end. The pivotable section is configured to pivot from a first closed position to a second open position. In the second open position, a passage is formed between the pivotable section and the center tube. The passage is configured to provide access to position a longitudinal member within the telescopic insertion assembly.

According to this invention, there is also provided an insertion assembly for penetrating vertebral bodies. The insertion assembly includes a cannula having an inner passage, an obturator configured for substantial housing within the passage of the cannula and a depth stop attached to the cannula. The depth stop is configured as a marker to indicate the insertion depth of the insertion device.

Various objects and advantages will become apparent to those skilled in the art from the following detailed description of the preferred embodiments, when read in light of the accompanying drawings.

BRIEF DESCRIPTION OF THE DRAWINGS

FIG. 11 is a perspective view in cross section of a portion of one of the plurality of the vertebra screw insertion assemblies illustrated in FIG. 10 together with a rod holder for initially positioning the alignment rod relative to the vertebra insertion assemblies.

FIG. 12 is a sectional elevational view taken along line 12-12 of FIG. 11.

FIG. 13 is a perspective view similar to FIG. 11 of a portion of one of the plurality of the vertebra screw insertion assemblies, the rod holder, and a centralizer for finally positioning the alignment rod relative to the vertebra screw insertion assemblies.

FIG. 14 is a sectional elevational view taken along line 14-14 of FIG. 13.

FIG. 17 is a perspective view of a first embodiment of the alignment rod illustrated in FIGS. 10 through 16.

FIG. 18 is a perspective view of a second embodiment of the alignment rod illustrated in FIGS. 10 through 16.

DETAILED DESCRIPTION OF THE PREFERRED EMBODIMENTS

Figure 1:
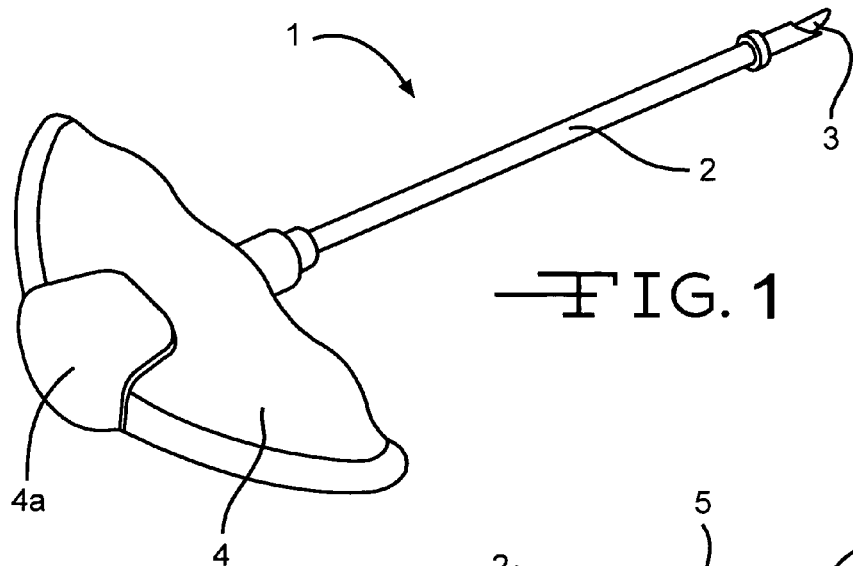
FIG. 1 is a perspective view of a first embodiment of a vertebra penetration device in accordance with this invention.

Referring now to the drawings, there is illustrated in FIG. 1 a first embodiment of a vertebra penetration device, indicated generally at 1, in accordance with this invention. The vertebra penetration device 1 is adapted to penetrate a vertebral body for a purpose that will be explained below. For example, the vertebra penetration device 1 can penetrate a vertebral body to form a bone tunnel for use in a surgical procedure. The illustrated vertebra penetration device 1 is a Jamshidi needle. However, the vertebra penetration device 1 can be embodied as any other structure.

The illustrated vertebra penetration device 1 includes a cannula 2, an obturator 3 that is slidably disposed within the cannula 2, and a handle 4. The handle 4 may include a removable portion 4a, although such is not required. The removable portion 4a of the handle 4 may be connected to the obturator 3 such that removal of the removable portion 4a causes removal of the obturator 3 from the cannula 2.

Figure 2:
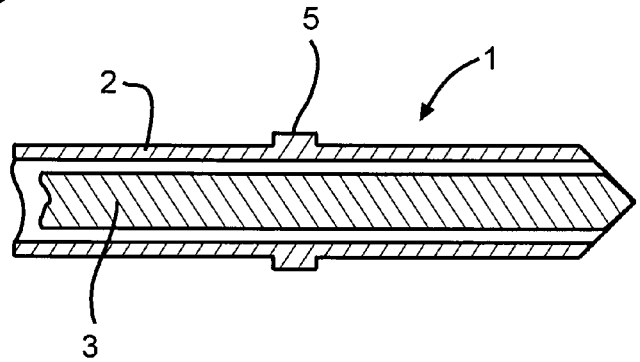
FIG. 2 is a cross-sectional view of a portion of the first embodiment of the penetration device illustrated in FIG. 1.

Referring now to FIG. 2, a portion of the vertebra penetration device 1 is illustrated in detail. As shown therein, the illustrated cannula 2 is generally hollow and cylindrical in shape. However, the cannula 2 can have any other desired shape or combination of shapes. The obturator 3 extends through interior of the cannula 2 and is supported for sliding movement relative thereto in any conventional manner. The outer surface of the cannula 2 has a depth indicator 5 provided therein. The depth indicator 5 can be embodied as any structure that can function as a marker to indicate the insertion depth of the cannula 2 within a vertebra during a surgical procedure. During such a surgical procedure, conventional imaging techniques, such as X-rays and the like, can be used to determine the location of the depth indicator 5 relative to the vertebra, thereby clearly indicating how far the cannula 2 has been inserted in the vertebra. The depth indicator 5 can be positioned at any desired predetermined distance from an end of the cannula 2 for this purpose.

In the illustrated embodiment, the depth indicator 5 has a generally rectangular cross sectional shape, having side walls that extend generally perpendicularly outwardly relative to the outer surface of the cannula 2 and an outer surface that extends generally concentrically relative to the outer surface of the cannula 2. However, the depth indicator 5 may be formed having any desired cross sectional shape or size that protrudes outwardly from the outer surface of the cannula 2. In the illustrated embodiment, the depth indicator 5 extends continuously about the outer surface of the cannula 2. However, the depth indicator 5 can be formed as one or more segments that extend about the outer surface of the cannula 2 in a non-continuous manner. The illustrated depth indicator 5 may be formed integrally with the remainder of the cannula 2 or may be formed from a separate piece that is secured thereto.

Figure 3:
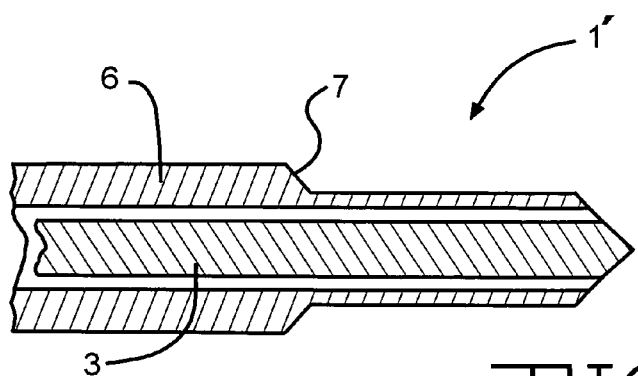
FIG. 3 is a cross-sectional view of a portion of a second embodiment of the penetration device illustrated in FIG. 1.

FIG. 3 illustrates a portion of a second embodiment of a vertebra penetration device, indicated generally at 1'. This second embodiment of the vertebra penetration device 1' includes a modified cannula 6 that supports the obturator 3 for sliding movement therein. The cannula 6 has first and second dimensional portions that define a modified depth indicator 7 therebetween. The first and second dimensional portions of the cannula 6 can have any desired shapes or sizes that define the depth indicator 7. Similarly, the depth indicator 7 can have any desired shape or combination of shapes. The depth indicator 7 functions in the same manner as described above in connection with the depth indicator 5 to clearly indicate how far the cannula 2 has been inserted in the vertebra during a surgical procedure.

Figure 4:
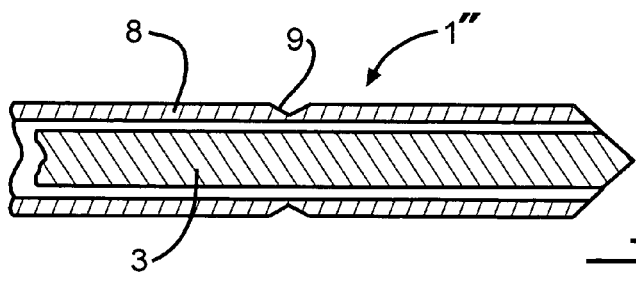
FIG. 4 is a cross-sectional view of a portion of a third embodiment of the penetration device illustrated in FIG. 1.

FIG. 4 illustrates a portion of a third embodiment of a vertebra penetration device, indicated generally at 1". This third embodiment of the vertebra penetration device 1" includes a modified cannula 8 that supports the obturator 3 for sliding movement therein. The outer surface of the cannula 8 has a depth indicator 9 provided therein. In the illustrated embodiment, the depth indicator 9 has a generally triangular cross sectional shape, having side walls that extend inwardly at an non-perpendicular angle relative to the outer surface of the cannula 8. However, the depth indicator 9 may be formed having any desired cross sectional shape or size that extends inwardly from the outer surface of the cannula 8. The depth indicator 9 functions in the same manner as described above in connection with the depth indicator 5 to clearly indicate how far the cannula 2 has been inserted in the vertebra during a surgical procedure.

Figure 5:
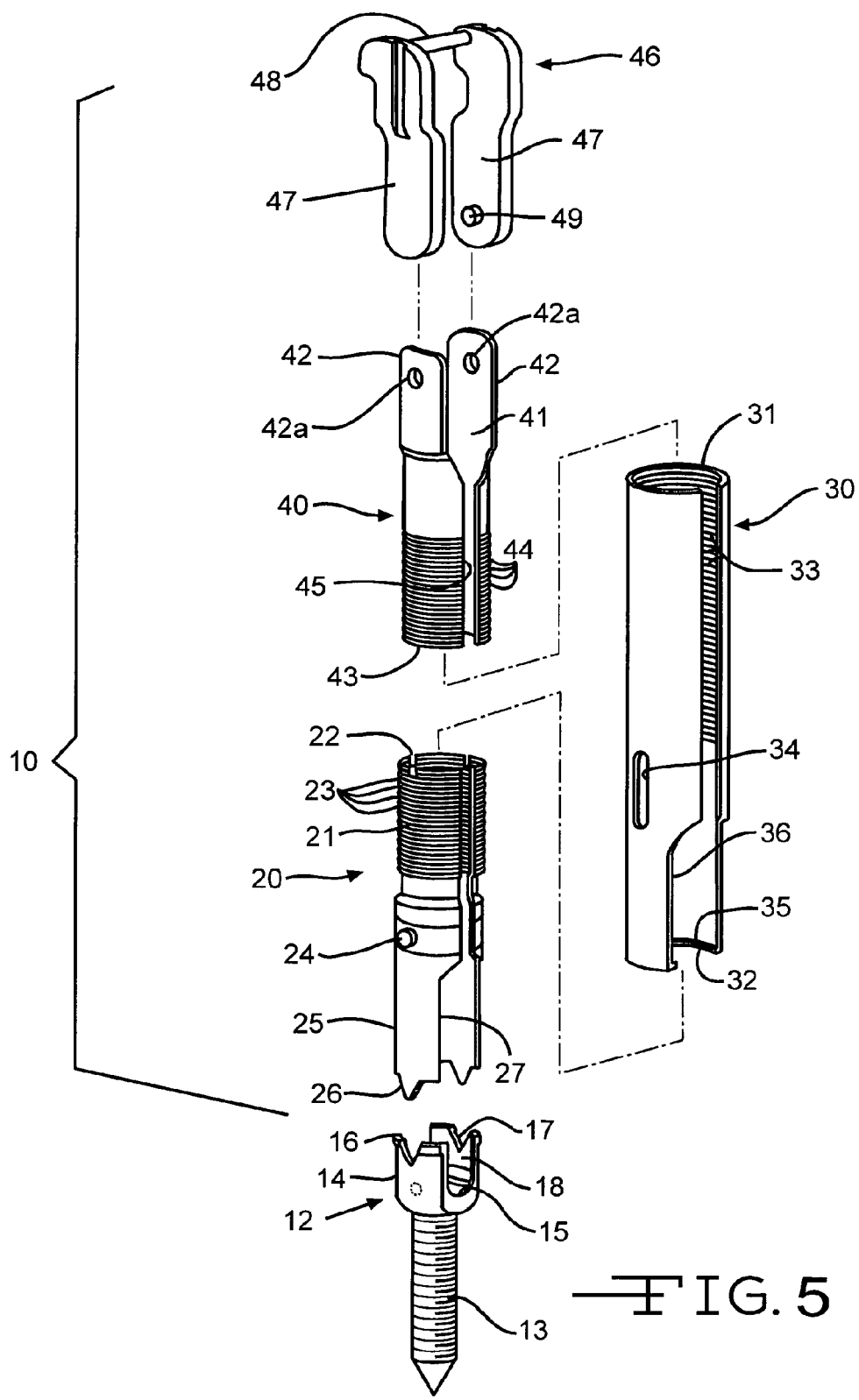
FIG. 5 is an exploded perspective view of a first embodiment of a vertebra screw insertion assembly in accordance with this invention.

Referring now to FIG. 5, there is illustrated a first embodiment of a vertebra screw insertion assembly 10 in accordance with this invention. The vertebra screw insertion assembly 10 is adapted to facilitate the securement of a pedicle screw 12 in a hole formed in a vertebra during a spinal surgical procedure (the hole being initially formed by the vertebra penetration device 1 described above). As will be explained in detail below, the axial length of the vertebra screw insertion assembly 10 is adjustable to facilitate its use with patients of differing sizes and shapes.

The pedicle screw 12 is conventional in the art and is adapted to be inserted into a vertebra (not shown) in any known manner. The illustrated pedicle screw 12 includes a threaded portion 13 and a head portion 14. The threaded portion 13 is configured for insertion into the vertebra and can have any desired root diameter, thread diameter, pitch, and number of threads. The head portion 14 includes a generally U-shaped yoke 15, a retainer structure 16, a pair of generally V-shaped drive slots 17, and an internally threaded portion 18 (for purposes of clarity, the threads of the internally threaded portion 18 are not shown). The pedicle screw 12 can be formed from any desired material.

The vertebra screw insertion assembly 10 also includes a lower portion indicated generally at 20. The lower portion 20 is generally hollow and cylindrical in shape, although such is not required. The lower portion 20 has an upper end 21 having a plurality of drive structures 22 provided therein. In the illustrated embodiment, the drive structures 22 are embodied as a plurality of slots extending downwardly from the upper end 21 of the lower portion 20. However, the drive structures 22 may be embodied as any desired structure. The purpose for the drive structures 22 will be explained below. In the illustrated embodiment, the outer surface of the upper end 21 of the lower portion 20 is formed having a plurality of axial retaining structures 23. The illustrated axial retaining structures 23 are a series of concentric annular protrusions. However, the axial retaining structures 23 may be embodied as any desired structure or series of structures. Alternatively, the axial retaining structures 23 may be omitted and a smooth outer surface be provided if desired.

The lower portion 20 also has an outwardly extending protrusion 24 provided therein. In the illustrated embodiment, the outwardly extending protrusion 24 is embodied as a hollow cylindrical protrusion. However, the outwardly extending protrusion 24 may be embodied as any desired structure. Alternatively, the outwardly extending protrusion 24 may be omitted if desired. The purpose for the outwardly extending protrusion 24 will be explained below.

The lower portion 20 further has a lower end 25 having a plurality of drive structures 26 provided therein. In the illustrated embodiment, the drive structures 26 are embodied as a plurality of generally V-shaped extensions extending downwardly from the lower end 25 of the lower portion 20. However, the drive structures 26 may be embodied as any desired structure. The purpose for the drive structures 26 will be explained below. Lastly, the lower portion 20 of the vertebra screw insertion assembly 10 has a slot 27 extending axially throughout the length thereof. The purpose for the slot 27 will be explained below.

The vertebra screw insertion assembly 10 also includes an intermediate portion indicated generally at 30. The intermediate portion 30 is generally hollow and cylindrical in shape, although such is not required. The intermediate portion 30 has an upper end 31 and a lower end 32. In the illustrated embodiment, the inner surface of the upper end 31 of the intermediate portion 30 is formed having a plurality of axial retaining structures 33. The illustrated axial retaining structures 33 are a series of concentric annular protrusions. However, the axial retaining structures 33 may be embodied as any desired structure or series of structures. Alternatively, the axial retaining structures 33 may be omitted and a smooth inner surface be provided if desired.

The intermediate portion 30 also has a slot 34 provided therein. In the illustrated embodiment, the slot 34 is elongated and extends generally axially. However, the slot 34 may have any desired shape. Alternatively, the slot 34 may be omitted if desired. The purpose for the slot 34 will be explained below.

The lower end 32 of the intermediate portion 30 has a retaining structure 35 provided therein. In the illustrated embodiment, the retaining structure 35 is embodied as a lip that extends inwardly about the lower end 32 of the intermediate portion 30. However, the retaining structure 35 may be embodied as any desired structure. The purpose for the retaining structure 35 will be explained below. Lastly, the intermediate portion 30 of the vertebra screw insertion assembly 10 has a slot 36 extending axially throughout the length thereof. The purpose for the slot 36 will be explained below.

The vertebra screw insertion assembly 10 also includes an upper portion indicated generally at 40. The upper portion 40 is generally hollow and cylindrical in shape, although such is not required. The upper portion 40 has an upper end 41 having a plurality of arms 42 provided therein. Each of the arms 42 has an opening 42a formed therethrough, although such is not required. The arms 42 may be embodied as any desired structure. The purpose for the arms 42 will be explained below. The upper portion 40 further has a lower end 43. In the illustrated embodiment, the outer surface of the lower end 43 of the upper portion 40 is formed having a plurality of axial retaining structures 44. The illustrated axial retaining structures 44 are a series of concentric annular protrusions. However, the axial retaining structures 44 may be embodied as any desired structure or series of structures. Alternatively, the axial retaining structures 44 may be omitted and a smooth outer surface be provided if desired. Lastly, the upper portion 40 of the vertebra screw insertion assembly 10 has a slot 45 extending axially throughout the length thereof. The purpose for the slot 45 will be explained below.

Lastly, the vertebra screw insertion assembly 10 includes an alignment bracket, indicated generally at 46. The illustrated alignment bracket 46 includes a pair of bracket arms 47 that are connected together by an transverse bar 48. Each of the bracket arms 47 has an inwardly extending protrusion 49 (only one is illustrated) provided thereon. However, the alignment bracket 46 may have any desired shape. The purpose for the alignment bracket 46 will be explained below.

Figure 6:
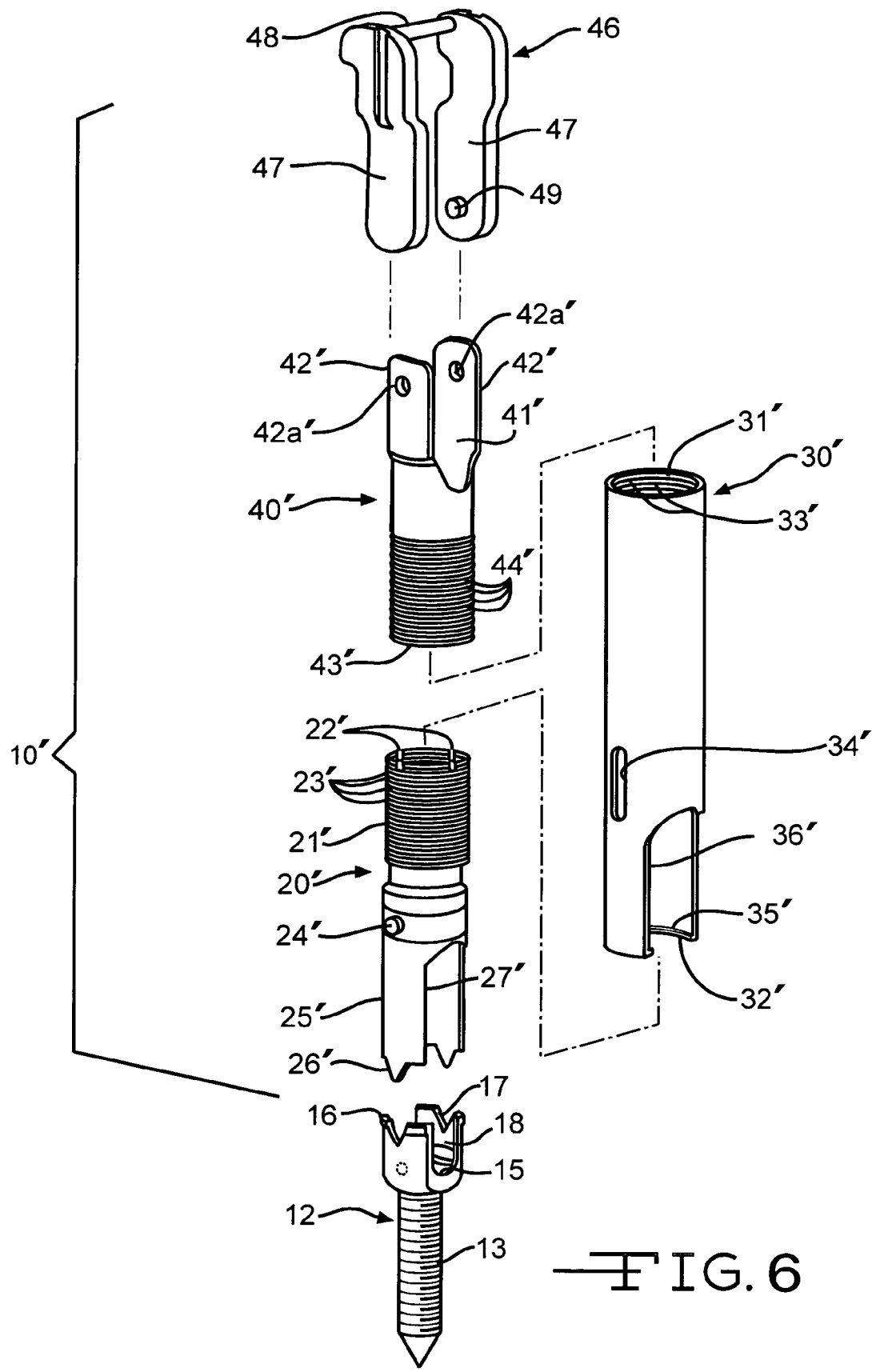
FIG. 6 is an exploded perspective view of a second embodiment of a vertebra screw insertion assembly in accordance with this invention.

Referring now to FIG. 6, there is illustrated a second embodiment of a vertebra screw insertion assembly 10' in accordance with this invention. The second embodiment of a vertebra screw insertion assembly 10' is similar to the first embodiment 10 described above, and like reference numbers are used to identify similar structures. As will be explained in detail below, the axial length of the vertebra screw insertion assembly 10' is also adjustable to facilitate its use with patients of differing sizes and shapes.

The vertebra screw insertion assembly 10' includes a lower portion indicated generally at 20'. The lower portion 20' is generally hollow and cylindrical in shape, although such is not required. The lower portion 20' has an upper end 21' having a plurality of drive structures 22' provided therein. In the illustrated embodiment, the drive structures 22' are embodied as a plurality of slots extending downwardly from the upper end 21' of the lower portion 20'. However, the drive structures 22' may be embodied as any desired structure. The purpose for the drive structures 22' will be explained below. In the illustrated embodiment, the outer surface of the upper end 21' of the lower portion 20' is formed having a plurality of axial retaining structures 23'. The illustrated axial retaining structures 23' are a series of concentric annular protrusions. However, the axial retaining structures 23' may be embodied as any desired structure or series of structures. Alternatively, the axial retaining structures 23' may be omitted and a smooth outer surface be provided if desired.

The lower portion 20' also has an outwardly extending protrusion 24' provided therein. In the illustrated embodiment, the outwardly extending protrusion 24' is embodied as a hollow cylindrical protrusion. However, the outwardly extending protrusion 24' may be embodied as any desired structure. Alternatively, the outwardly extending protrusion 24' may be omitted if desired. The purpose for the outwardly extending protrusion 24' will be explained below.

The lower portion 20' further has a lower end 25' having a plurality of drive structures 26' provided therein. In the illustrated embodiment, the drive structures 26' are embodied as a plurality of generally V-shaped extensions extending downwardly from the lower end 25' of the lower portion 20'. However, the drive structures 26' may be embodied as any desired structure. The purpose for the drive structures 26' will be explained below. Lastly, the lower portion 20' of the vertebra screw insertion assembly 10' has a slot 27' extending axially throughout only a portion of the length thereof. The purpose for the slot 27' will be explained below.

The vertebra screw insertion assembly 10' also includes an intermediate portion indicated generally at 30'. The intermediate portion 30' is generally hollow and cylindrical in shape, although such is not required. The intermediate portion 30' has an upper end 31' and a lower end 32'. In the illustrated embodiment, the inner surface of the upper end 31' of the intermediate portion 30' is formed having a plurality of axial retaining structures 33'. The illustrated axial retaining structures 33' are a series of concentric annular protrusions. However, the axial retaining structures 33' may be embodied as any desired structure or series of structures. Alternatively, the axial retaining structures 33' may be omitted and a smooth inner surface be provided if desired.

The intermediate portion 30' also has a slot 34' provided therein. In the illustrated embodiment, the slot 34' is elongated and extends generally axially. However, the slot 34' may have any desired shape. Alternatively, the slot 34' may be omitted if desired. The purpose for the slot 34' will be explained below.

The lower end 32' of the intermediate portion 30' has a retaining structure 35' provided therein. In the illustrated embodiment, the retaining structure 35' is embodied as a lip that extends inwardly about the lower end 32' of the intermediate portion 30'. However, the retaining structure 35' may be embodied as any desired structure. The purpose for the retaining structure 35' will be explained below. Lastly, the intermediate portion 30' of the vertebra screw insertion assembly 10 has a slot 36' extending axially throughout only a portion the length thereof. The purpose for the slot 36' will be explained below.

The vertebra screw insertion assembly 10' also includes an upper portion indicated generally at 40'. The upper portion 40' is generally hollow and cylindrical in shape, although such is not required. The upper portion 40' has an upper end 41' having a plurality of arms 42' provided therein. Each of the arms 42' has an opening 42a' formed therethrough, although such is not required. The arms 42' may be embodied as any desired structure. The purpose for the arms 42' will be explained below. The upper portion 40' further has a lower end 43'. In the illustrated embodiment, the outer surface of the lower end 43' of the upper portion 40' is formed having a plurality of axial retaining structures 44'. The illustrated axial retaining structures 44' are a series of concentric annular protrusions. However, the axial retaining structures 44' may be embodied as any desired structure or series of structures. Alternatively, the axial retaining structures 44' may be omitted and a smooth outer surface be provided if desired.

Lastly, the vertebra screw insertion assembly 10' includes an alignment bracket, indicated generally at 46. The illustrated alignment bracket 46 is the same as described above in connection with the vertebra screw insertion assembly 10. The purpose for the alignment bracket 46 will be explained below.

Figure 7:
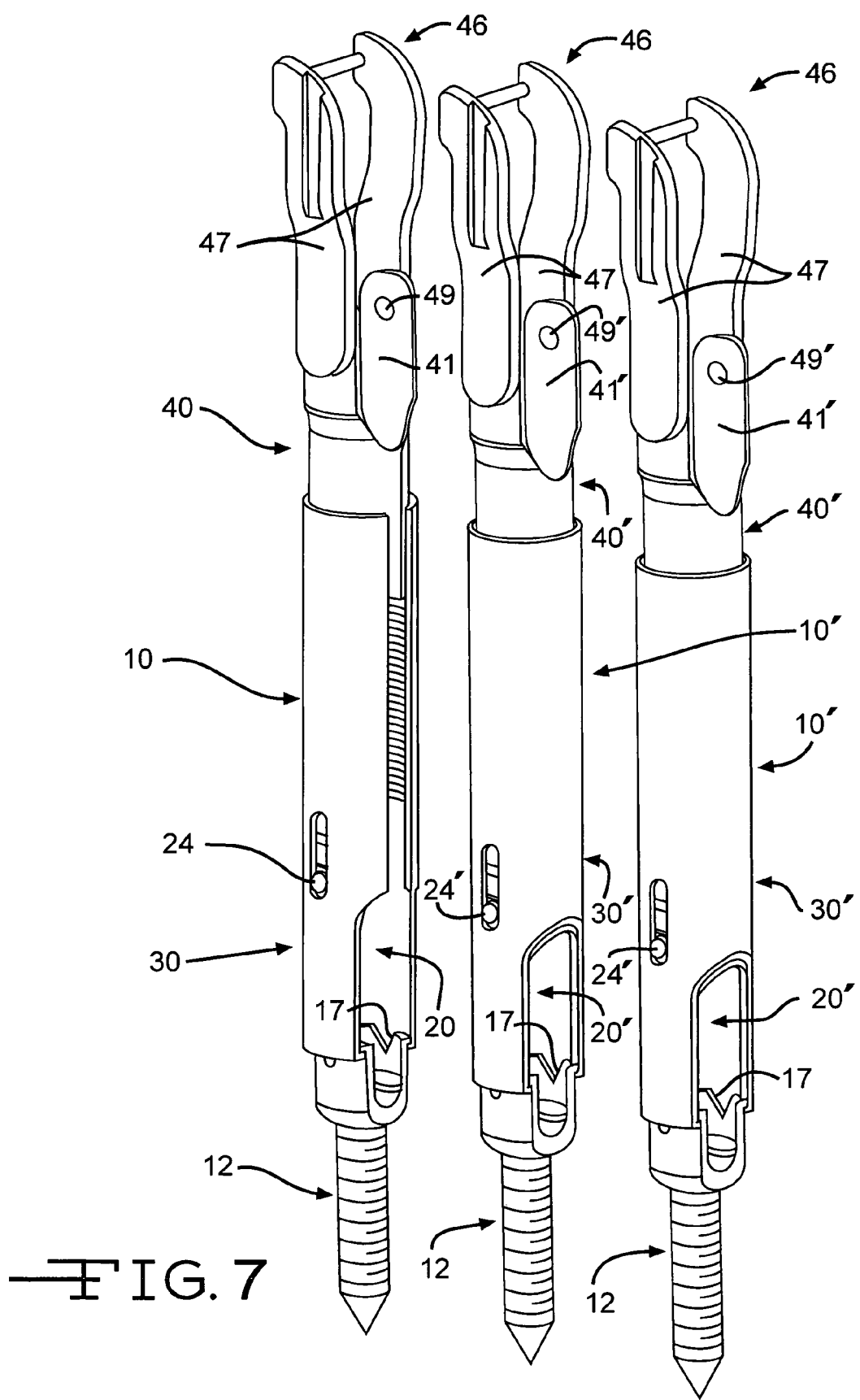
FIG. 7 is a perspective view of a plurality of vertebra screw insertion assemblies shown in an initial orientation.

FIG. 7 shows the first embodiment of the vertebra screw insertion assembly 10 in an initial orientation. As shown therein, the lower portion 20 of the vertebra screw insertion assembly 10 is disposed within the intermediate portion 30 thereof such that the protrusion 24 is received within the slot 34. The retaining structure 16 of the pedicle screw 12 engages the retaining lip 35 provided on the intermediate portion 30 of the vertebra screw insertion assembly 10, and the generally V-shaped extensions 26 provided on the lower end 25 of the lower portion 20 are received within the generally V-shaped drive slots 17 of the pedicle screw 12. Thus, in a manner that is known in the art, rotation of the lower portion 20 of the vertebra screw insertion assembly 10 (which can be accomplished by means of a conventional tool (not shown) that engages the drive slots 22 causes rotation of the pedicle screw 12. Accordingly, the pedicle screw 12 can be threaded into a bone tunnel, such as might be formed by the vertebra penetration device 1 described above. The retaining bracket 46 is pivotably connected to the upper end 42 of the upper portion 40 of the vertebra screw insertion assembly 10. This can be accomplished by inserting the inwardly extending protrusions 49 provided on the bracket arms 47 into the openings 42a provided on the arms 42 of the upper end 41 of the upper portion 40.

The axial length of the vertebra screw insertion assembly 10 is adjustable to facilitate its use with patients of differing sizes and shapes. This is done so that a minimum amount of the vertebra screw insertion assembly 10 will extend outwardly from the patient, thereby providing a maximum amount of clearance in the surgical field above the skin of the patient. As discussed above, the lower end 43 of the upper portion 40 of the vertebra screw insertion assembly 10 is received axially within the upper end 31 of the intermediate portion 30 thereof. The upper portion 40 of the vertebra screw insertion assembly 10 can thus be axially positioned relative to the intermediate portion 30 thereof by moving the upper portion 40 to a desired position relative to the intermediate portion 30. This can be accomplished manually, by means of a tool (not shown), or any other means. When so positioned, the upper portion 40 of the vertebra screw insertion assembly 10 is located in a desired axial position relative to the intermediate portion 30 thereof based upon the size and shape of the patient.

In order to retain the upper portion 40 of the vertebra screw insertion assembly 10 in the desired axial position relative to the intermediate portion 30 thereof, the illustrated plurality of axial retaining structures 44 provided on the outer surface of the lower end 43 of the upper portion 40 engages the corresponding plurality of axial retaining structures 33 provided on the inner surface of the upper end 31 of the intermediate portion 30. In this manner, a desired axial length of the vertebra screw insertion assembly 10 can be achieved and retained for further use, as described below. As mentioned above, however, the axial retaining structures 33 and 44 may be embodied as any other desired structure or series of structures. Alternatively, the axial retaining structures 33 and 44 may be omitted and smooth surfaces can be provided if desired. All that is necessary is that the axial length of the vertebra screw insertion assembly 10 be adjustable to facilitate its use with patients of differing sizes and shapes.

FIG. 7 also shows two of the second embodiment of the vertebra screw insertion assemblies 10' in an initial orientation. The arrangement of the various elements of the second embodiment of the vertebra screw insertion assemblies 10' is the same as described above in connection with the first embodiment of the vertebra screw insertion assembly 10. In the same manner as described above, and for the same reason, the axial lengths of the vertebra screw insertion assemblies 10 are adjustable to facilitate their use with patients of differing sizes and shapes.

As shown in FIG. 7, the slot 27 formed through the lower portion 20 of the vertebra screw insertion assembly 10, the slot 36 formed through the intermediate portion 30 of the vertebra screw insertion assembly 10, and the slot 45 formed through the upper portion 40 of the vertebra screw insertion assembly 10 are all axially aligned with one another to provide a continuous slot through the vertebra screw insertion assembly 10. As also shown in FIG. 7, this continuous slot through the vertebra screw insertion assembly 10 is oriented facing inwardly toward the adjacent one of the plurality of vertebra screw insertion assemblies 10'. The purpose for this continuous slot and the reason for its orientation in this manner will be described below.

Figure 8:
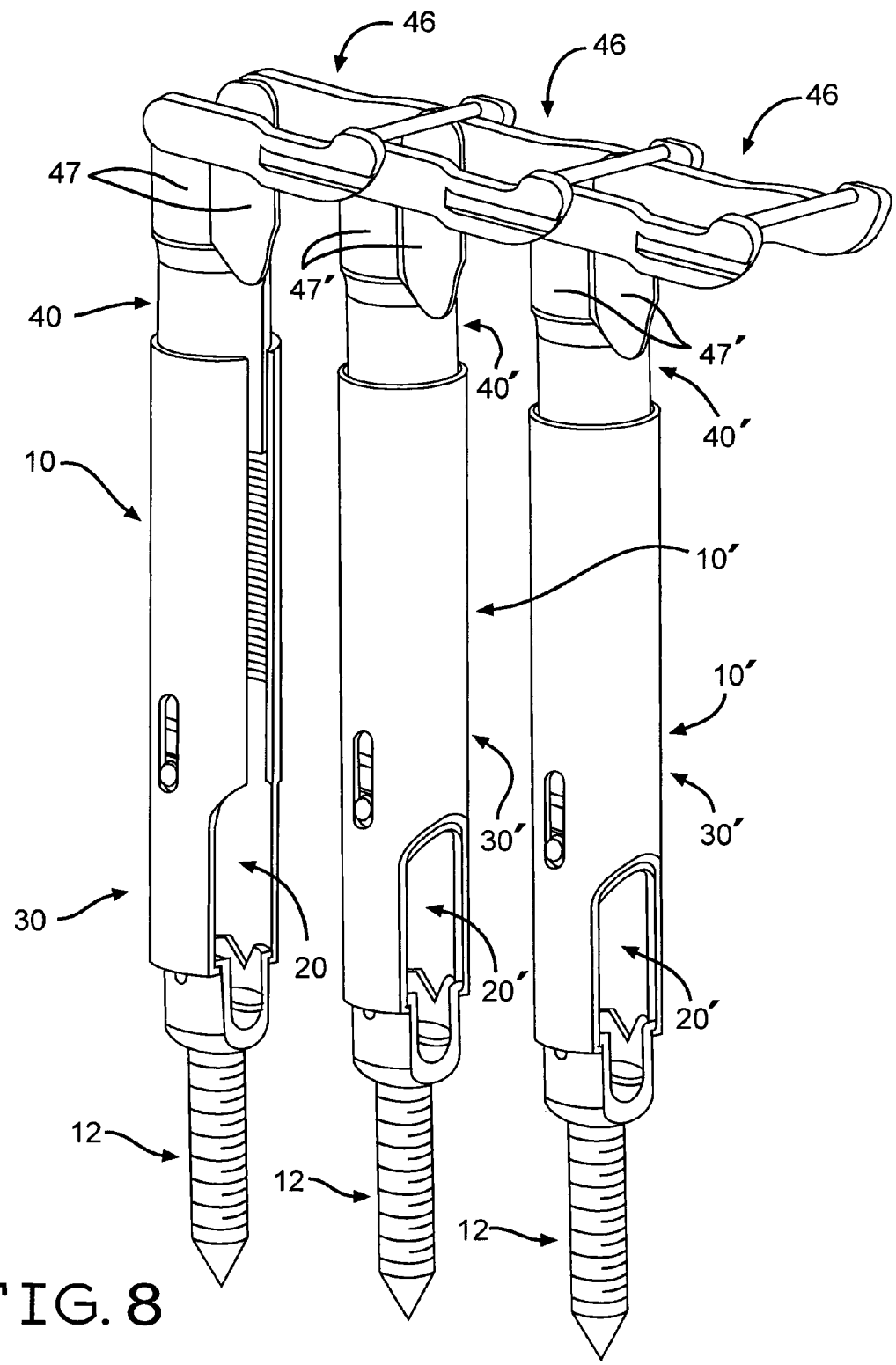
FIG. 8 is a perspective view of the plurality of vertebra screw insertion assemblies illustrated in FIG. 7 shown in an aligned orientation.

FIG. 8 shows the plurality of vertebra screw insertion assemblies 10 and 10' illustrated in FIG. 7 shown in an aligned orientation. This is accomplished by pivoting each of the alignment brackets 46 from the unaligned positions illustrated in FIG. 7 into the aligned positions illustrated in FIG. 8. In such aligned positions, the alignment bracket 46 provided on the vertebra screw insertion assembly 10 engages the alignment bracket 46 provided on the adjacent first vertebra screw insertion assembly 10. Similarly, the alignment bracket 46 provided on the first vertebra screw insertion assembly 10' engages the alignment bracket 46 provided on the adjacent second vertebra screw insertion assembly 10'. Any number of such vertebra screw insertion assemblies 10 and 10' may be aligned in this manner. In the illustrated embodiment, the alignment brackets 46 engage each other in a nested manner, although such is not required.

Figure 9:
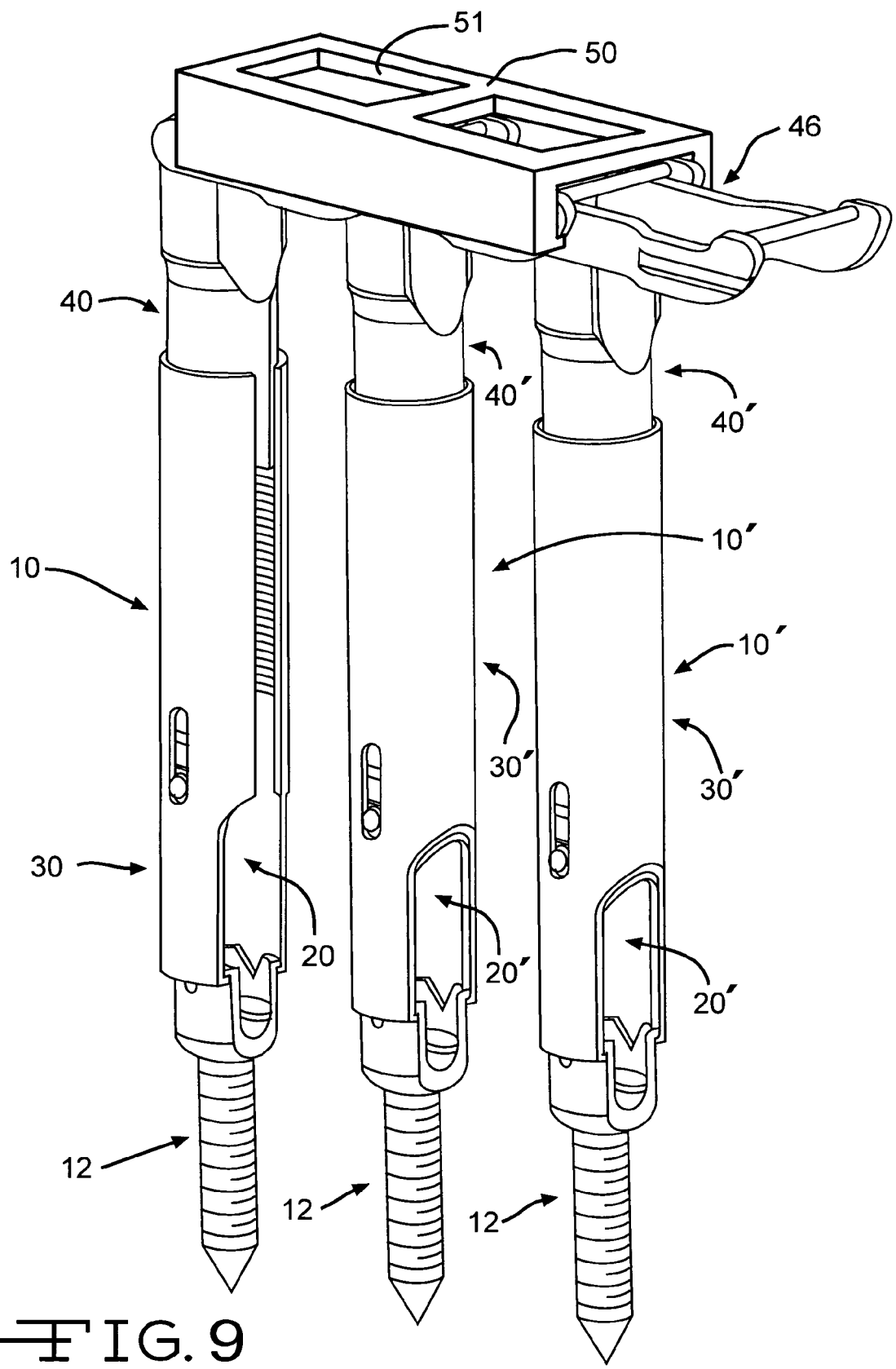
FIG. 9 is a perspective view of the plurality of vertebra screw insertion assemblies illustrated in FIG. 8 shown in an aligned and locked orientation.

FIG. 9 is a perspective view of the plurality of vertebra screw insertion assemblies illustrated in FIG. 8 shown in an aligned and locked orientation. To accomplish this, a locking bracket 50 is engaged with some or all of the alignment brackets 46 provided on the first and second vertebra screw insertion assemblies 10 and 10'. The locking bracket 50 is optional and may be embodied as any desired structure that is capable of engaging some or all of the alignment brackets 46 and for positively maintaining them in desired positions relative to one another. Preferably, the locking bracket 50 has at least one opening 51 formed therethrough (two are shown in the illustrated embodiment) for a purpose that will be explained below. When the locking bracket 50 is installed as shown in FIG. 9, the outer ends of the first and second vertebra screw insertion assemblies 10 and 10' are generally locked in alignment with one another.

Figure 10:
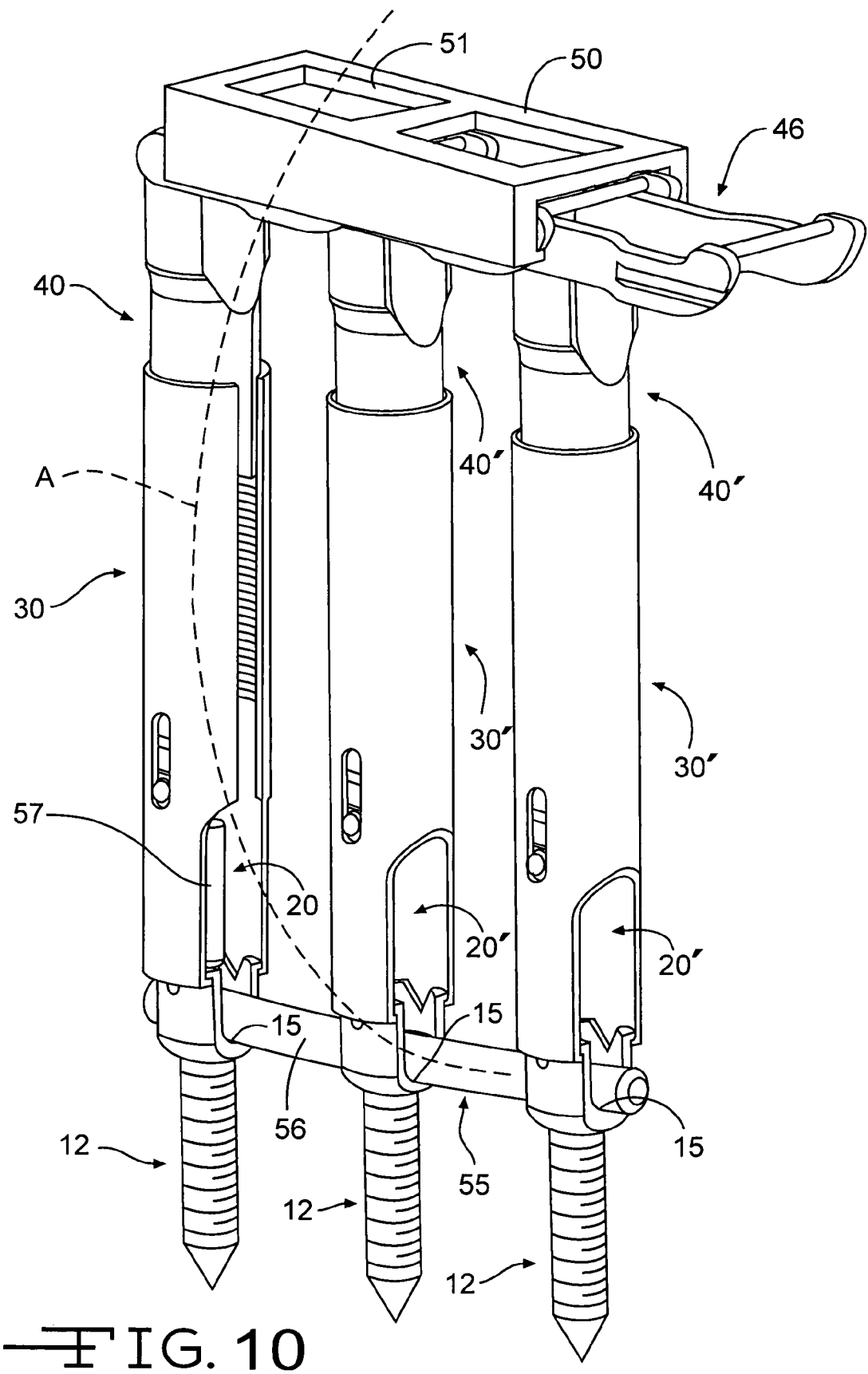
FIG. 10 is a perspective view of the plurality of vertebra screw insertion assemblies illustrated in FIG. 9 having an alignment rod installed therein.

Next, as shown in FIG. 10, an alignment rod 55 is installed in the first and second vertebra screw insertion assemblies 10 and 10'. The illustrated alignment rod 55 includes a body portion 56 having a positioning post 57 extending therefrom. The structure of the alignment rod 55 will be explained in greater detail below. The alignment rod 55 can be installed in the first and second vertebra screw insertion assemblies 10 and 10' along a path defined by the dotted line A in FIG. 10. As mentioned above, the slot 27 formed through the lower portion 20 of the vertebra screw insertion assembly 10, the slot 36 formed through the intermediate portion 30 of the vertebra screw insertion assembly 10, and the slot 45 formed through the upper portion 40 of the first vertebra screw insertion assembly 10 are all axially aligned with one another to provide a continuous slot through the first vertebra screw insertion assembly 10. The path defined by the dotted line A in FIG. 10 extends through this continuous slot. During insertion, portions of the alignment rod 55 pass through portions of the interior of the first vertebra screw insertion assembly 10. The continuous slot thus provides sufficient clearance for the alignment rod 55 to be installed in the first and second vertebra screw insertion assemblies 10 and 10'. When so installed, the body portion 56 of the alignment rod 55 is generally received within the generally U-shaped yokes 15 of the pedicle screws 12, and the positioning post 57 is generally received within the interior of the first vertebra screw insertion assembly 10.

After being installed, it is desirable to precisely position the alignment rod 55 relative to the first vertebra screw insertion assembly 10. This can be accomplished by means of a first positioning tool, indicated generally at 60 in FIG. 11. As shown therein, the first positioning tool 60 includes a handle 61 having a hollow interior 61a and an elongated shaft 62 that extends from the handle 61. A generally C-shaped slot 63 is formed through the handle 61 adjacent to the shaft 62. The lower end of the shaft 62 has a counterbore 64 formed therein. The first positioning tool 60 can be installed by inserting the shaft 62 downwardly through the first vertebra screw insertion assembly 10 such that the positioning post 57 of the alignment rod 55 is received within the counterbore 64. As best shown in FIG. 12, the positioning post 57 of the alignment rod 55 is preferably received snugly within the counterbore 64 of the first positioning tool 60 such that the alignment rod 55 and the first positioning tool 60 are precisely positioned relative to one another. Also, the positioning post 57 of the alignment rod 55 and the counterbore 64 of the first positioning tool 60 are formed having non-circular cross sectional shapes for a purpose that will be explained below.

Figure 15:
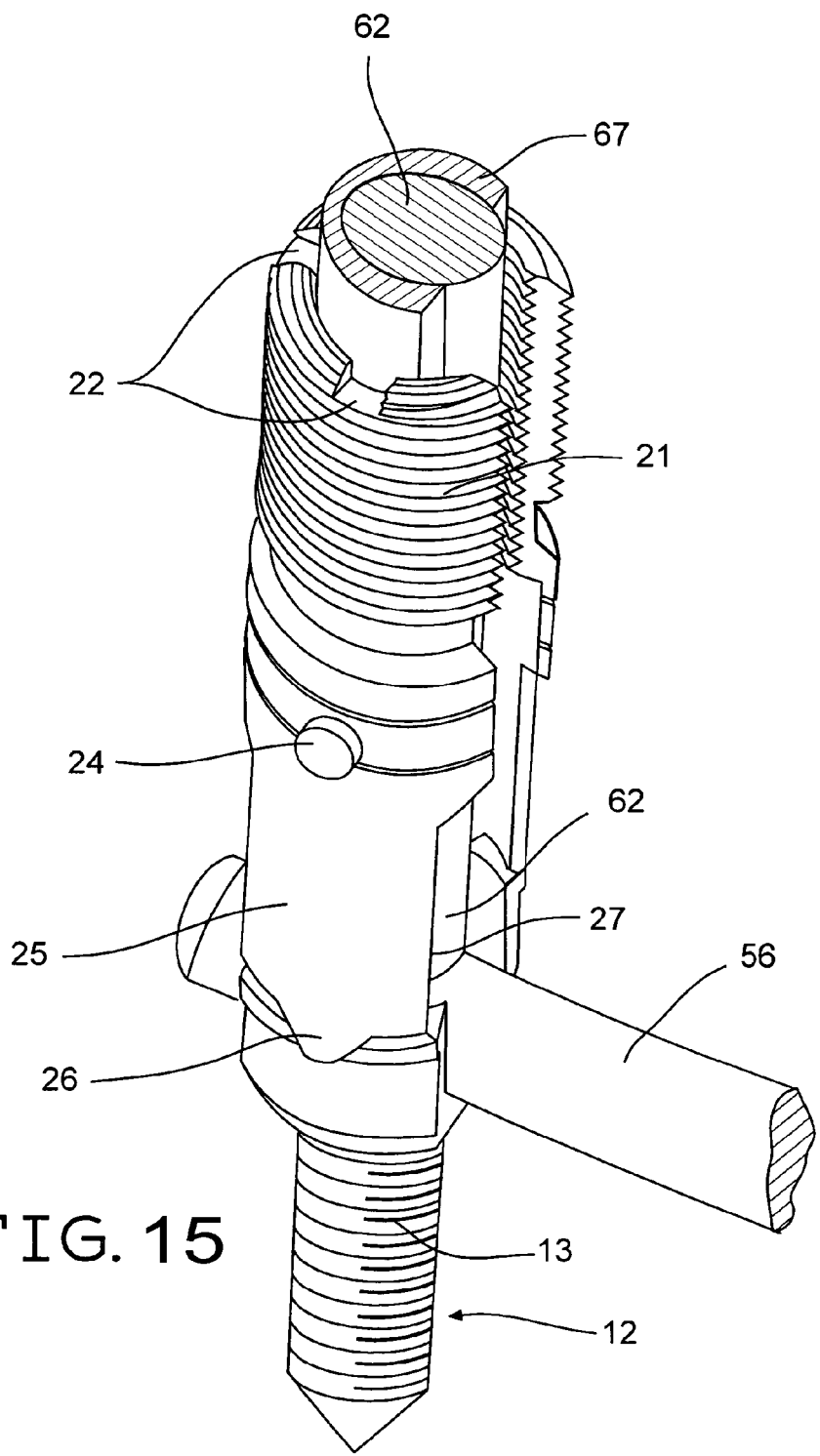
FIG. 15 is an enlarged perspective view of portions of the portion of one of the vertebra screw insertion assemblies, the rod holder, and the centralizer illustrated in FIGS. 13 and 14.

After the first positioning tool 60 has been installed, a second positioning tool, indicated generally at 65 in FIG. 13, is also installed. As shown therein, the second positioning tool 65 includes a handle 66 having an elongated generally C-shaped shaft 67 that extends therefrom. The generally C-shaped shaft 67 is sized and shaped so as to extend through the generally C-shaped slot 63 formed through the handle 61 and about the shaft 62 of the first positioning tool 60. As best shown in FIGS. 14 and 15, the generally C-shaped shaft 67 of the second positioning tool 65 is preferably received snugly between outer surface of the shaft 62 of the first positioning tool 60 and the inner surface of the lower member 20 of the first vertebra screw insertion assembly 10 such that the body portion 56 of the alignment rod 55 and the first vertebra screw insertion assembly 10 are precisely positioned relative to one another. Consequently, the alignment rod 55 is precisely positioned relative to the first and second vertebra screw insertion assemblies 10 and 10'.

Figure 16:
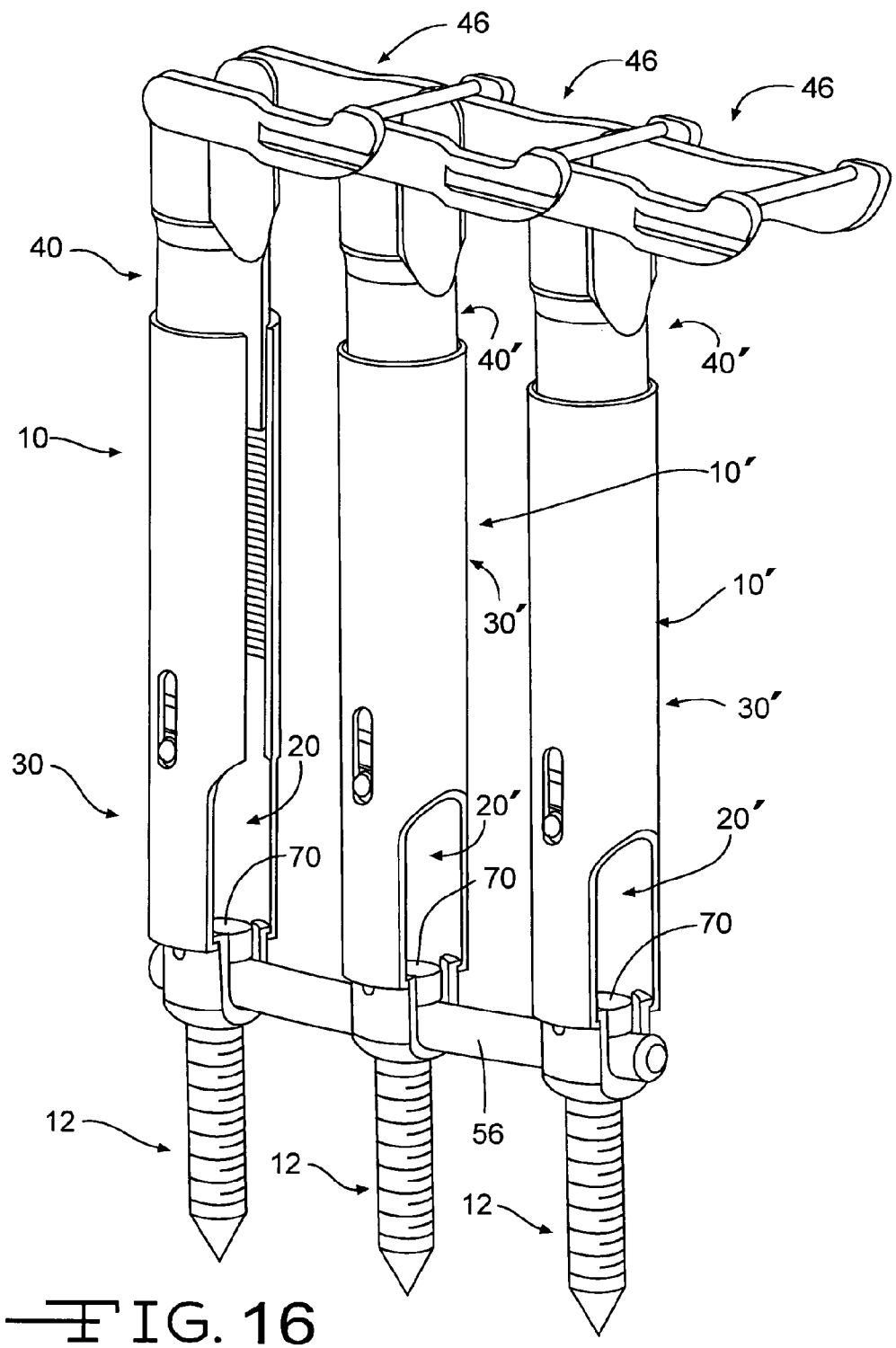
FIG. 16 is a perspective view of the plurality of the vertebra screw insertion assemblies, with the rod holder and the centralizer removed and with a plurality of retainers therein.

After being precisely positioned relative to the first and second vertebra screw insertion assemblies 10 and 10', the body portion 56 of the alignment rod 55 can be secured to each of the second vertebra screw insertion assemblies 10'. As shown in FIG. 16, this can be done by means of fasteners 70 that are threaded or otherwise secured to the generally U-shaped yokes 15 of the pedicle screws 12. The fasteners 70 are conventional in the art and are inserted through each of the second vertebra screw insertion assemblies 10' into engagement with the generally U-shaped yokes 15 of the pedicle screws 12. When secured thereto, the fasteners 70 precisely position the pedicle screws 12 relative to the body portion 56 of the alignment rod 55. As a result, the vertebrae to which each of the pedicle screws 12 are attached are positioned in accordance with the shape of the body portion 56 of the alignment rod 55.

Next, the second positioning tool 65 is removed from the first vertebra screw insertion assembly 10 by withdrawing it from the first positioning tool 60. Then, the first positioning tool 60 is removed from the first vertebra screw insertion assembly 10. The first positioning tool 60 can be used to remove the positioning post 57 from the alignment rod 55 by rotating the first positioning tool 60 before it is removed from the first vertebra screw insertion assembly 10. As mentioned above, the positioning post 57 of the alignment rod 55 and the counterbore 64 of the first positioning tool 60 are formed having non-circular cross sectional shapes. By rotating the first positioning tool 60 before it is removed from the first vertebra screw insertion assembly 10, the positioning post 57 can be snapped apart from the alignment rod 55, thereby facilitating its removal when the first positioning tool 60 is removed from the first vertebra screw insertion assembly 10. Thereafter, another fastener 70 can be threaded or otherwise secured to the generally U-shaped yoke 15 of the pedicle screw 12 to secure the first vertebra screw insertion assembly 10 into engagement with the generally U-shaped yoke 15 of the associated pedicle screw 12.

FIG. 17 illustrates the structure of the alignment rod 55 in detail. In this embodiment, the positioning post 57 and the body portion 56 of the alignment rod 55 are formed integrally from a single piece of material. As shown therein, a recessed area 58 may be provided between the positioning post 57 and the body portion 56 of the alignment rod 55 to facilitate the removal of the positioning post 57 from the body portion 56 as described above. Alternatively, as shown in FIG. 18, a modified positioning post 57' and a modified body portion 56' of an alignment rod 55 may be formed from separate pieces of material that are releasably connected together. For example, as shown therein, the modified positioning post 57' and the modified body portion 56' can have cooperating threaded portions 58' and 59' or other structures provided thereon that releasably connect them together.

Figures 19, 20, 21:
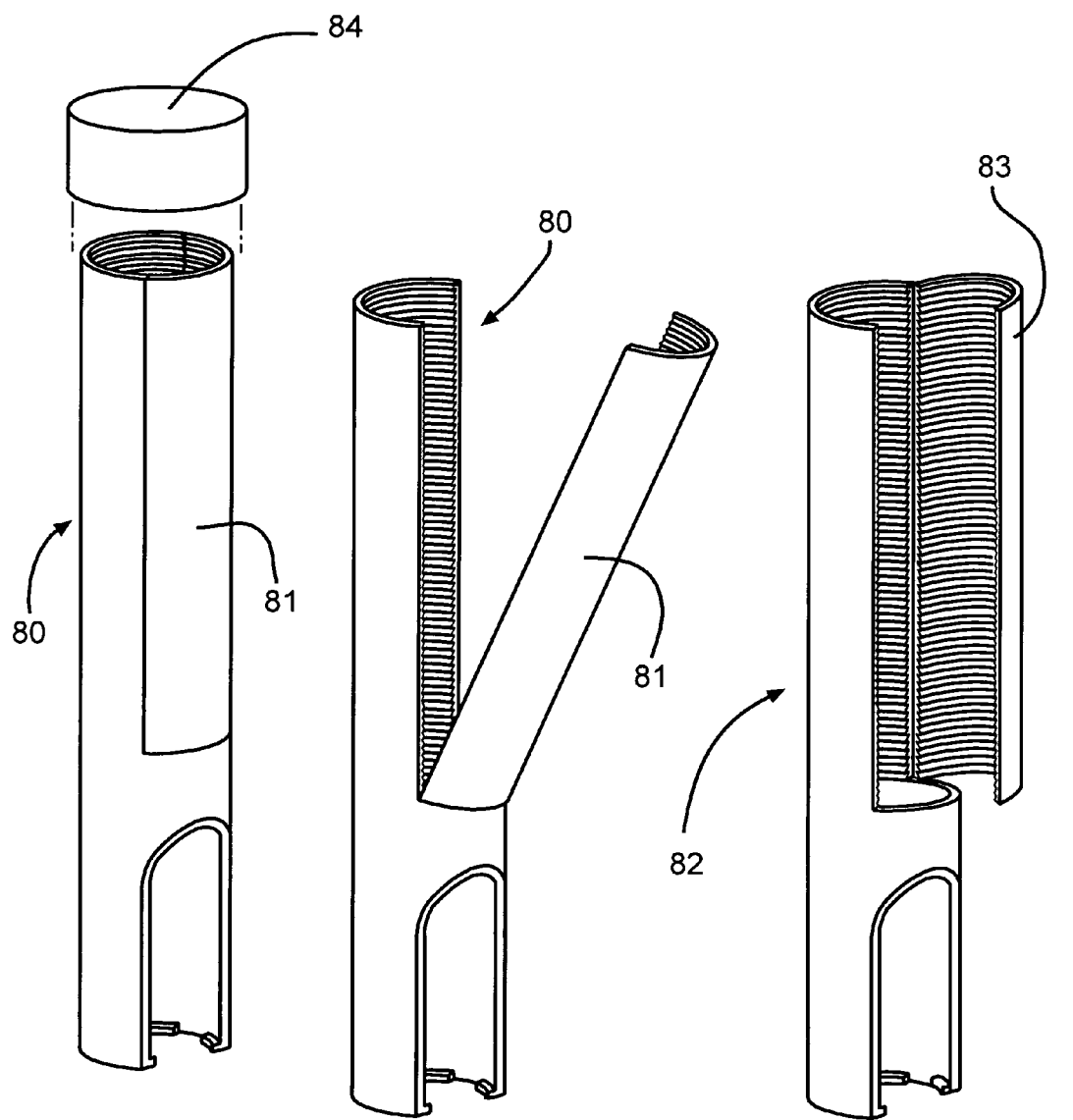
FIG. 19 is a perspective view of a second embodiment of an intermediate tube shown in a closed position.
FIG. 20 is a perspective view of the intermediate tube illustrated in FIG. 19 shown in an opened position.
FIG. 21 is a perspective view of a third embodiment of an intermediate tube shown in an opened position.

As discussed above, the intermediate portion 30 of the first vertebra screw insertion assembly 10 has a slot 36 extending axially throughout the length thereof to provide clearance for the alignment rod 55 to be installed in the first and second vertebra screw insertion assemblies 10 and 10'. In lieu of such slot 36, however, the intermediate portion 30 of the first vertebra screw insertion assembly 10 with a movable section. In a first modified embodiment of the intermediate portion, indicated generally at 80 in FIGS. 19 and 20, the slot 36 has been replaced by a section 81 that is movable relative to the intermediate portion 80 about an axis that is generally transverse to the axial orientation thereof. In a second modified embodiment of the intermediate portion, indicated generally at 82 in FIG. 21, the slot 36 has been replaced by a section 83 that is movable relative to the intermediate portion 80 about an axis that is generally parallel to the axial orientation thereof. In both embodiments, the movable sections 81 and 83 are sized and shaped to provide clearance for the alignment rod 55 to be installed in the first and second vertebra screw insertion assemblies 10 and 10'. In both instances, the movable sections 81 and 83 may be movably supported on the associated intermediate portions 80 and 82 by any desired hinge or other mechanism. Also, in both instances, the movable sections 81 and 83 may be positively maintained in engagement with the remainders of the intermediate portions 80 and 82 by a retainer cap 84 or any other desired structure.

Figure 22:
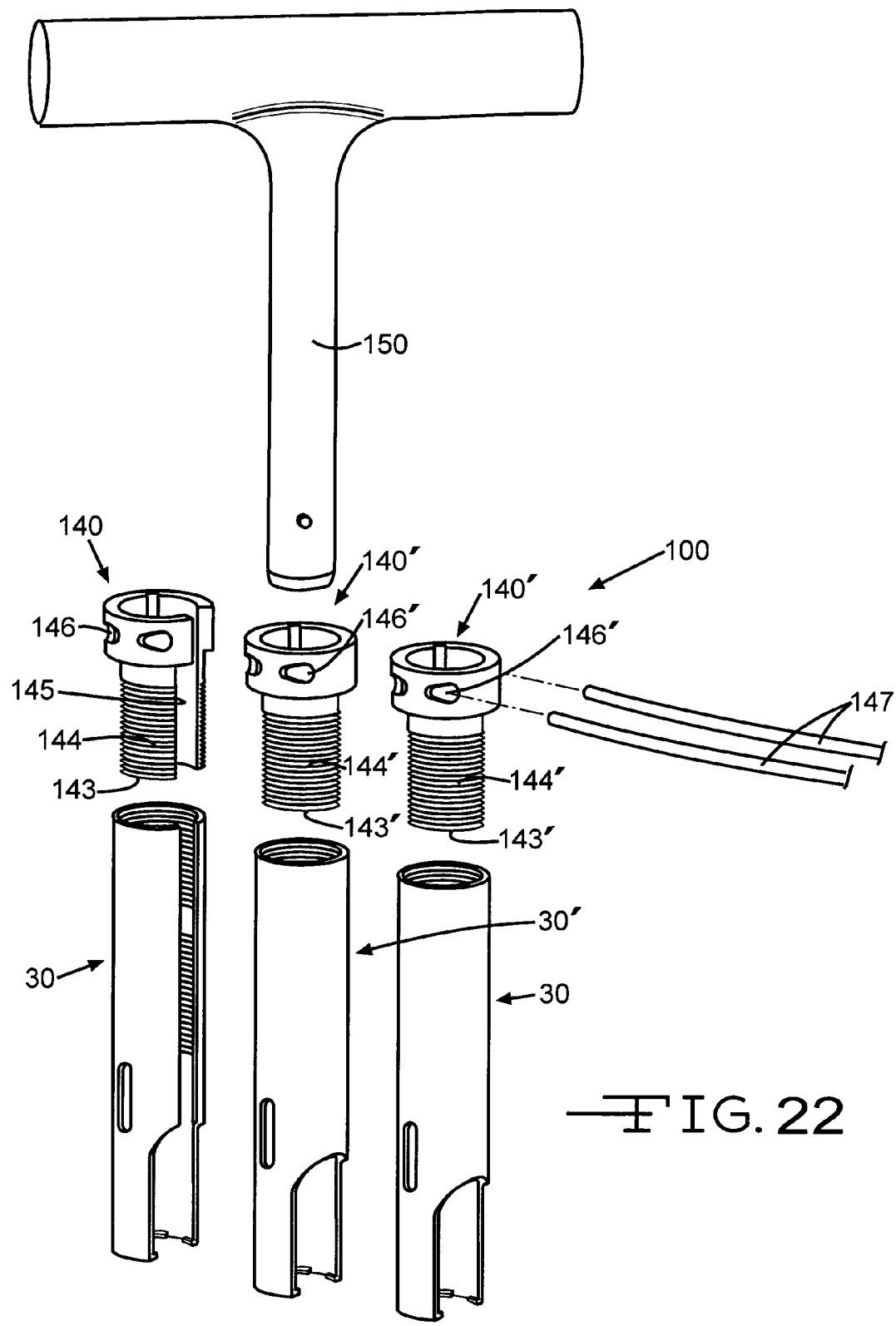
FIG. 22 is an exploded perspective view of a second embodiment of a vertebra screw insertion assembly in accordance with this invention.

FIG. 22 illustrates a portion of a second embodiment of a vertebra screw insertion assembly, indicated generally at 100, in accordance with this invention. In this modified embodiment, the upper portions 40 and 40' have been replaced with modified upper portions 140 and 140'. The outer surfaces of lower ends 143 and 143' of the upper portions 140 and 140' are respectively formed having pluralities of axial retaining structures 144 and 144', similar in structure and operation to the plurality of axial retaining structures 44 and 44' described above. Likewise, the upper portion 140 also has a slot 145 that is similar in structure and operation to the slot 45 described above. In this embodiment, however, the upper portions 140 and 140' additionally have one or more apertures 146 and 146' respectively formed therethrough. One or more alignment devices 147 can extend through these apertures 146 and 146' to align the vertebra screw insertion assemblies with one another, similar to the alignment brackets 46 discussed above. In use, the upper portions 140 and 140' are axially positioned at desired locations relative to the associated intermediate portions 30 and 30' in the same manner and for the same purpose as described above. If desired, a positioning tool 150 can be used to facilitate the axial positioning of the upper portions 140 and 140' at desired locations relative to the associated intermediate portions 30 and 30'.

Figure 23:
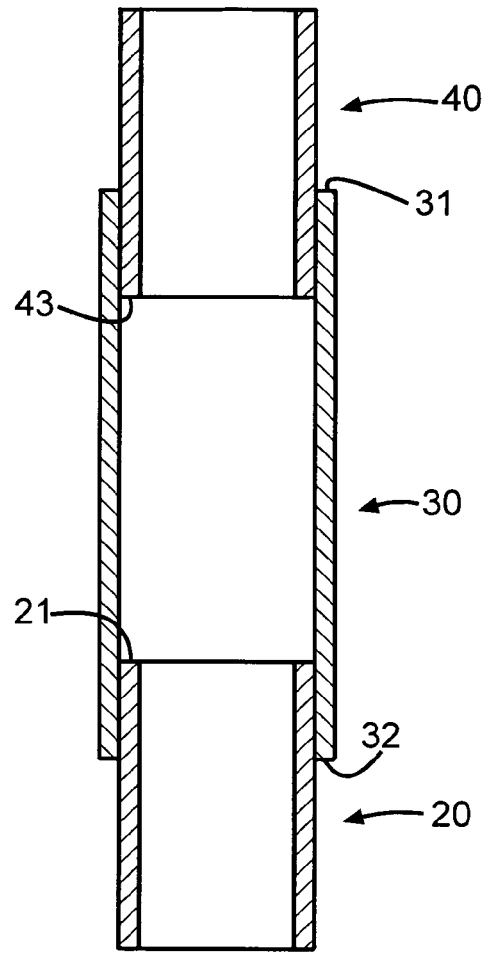
FIG. 23 is schematic sectional elevational view of portions of the first vertebra screw insertion assembly illustrated in FIG. 5.
Figure 24:
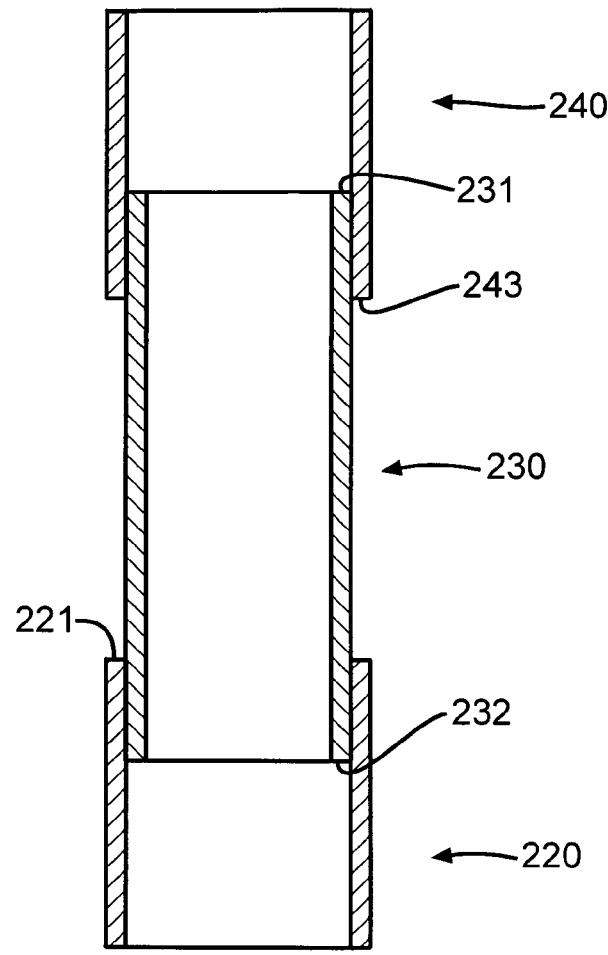
FIG. 24 is schematic sectional elevational view similar to FIG. 23 of an alternative arrangement of portions of the first vertebra screw insertion assembly illustrated in FIG. 5.

FIG. 23 is schematic sectional elevational view of portions of the first vertebra screw insertion assembly 10 illustrated in FIG. 5. As shown therein, the upper end 21 of the lower portion 20 is received axially within the lower end 32 of the intermediate portion 30, and the lower end 43 of the upper portion 40 is received axially within the upper end 31 of the intermediate portion 30. Alternatively, in a modified embodiment shown in FIG. 24, an upper end 221 of a lower portion 220 can be received axially about a lower end 232 of an intermediate portion 230, and a lower end 243 of an upper portion 240 can be received axially within an upper end 231 of the intermediate portion 230.

The above detailed description of the present invention is given for explanatory purposes. It will be apparent to those skilled in the art that numerous changes and modifications other than those cited can be made without departing from the scope of the invention. Accordingly, the whole of the foregoing description is to be construed in an illustrative and not a limitative sense, the scope of the invention being defined by the appended claims.

What is claimed is:

1. A pedicle screw insertion assembly comprising:
    a first portion that is generally hollow and cylindrical in shape and includes an axial retaining structure, a pedicle screw drive structure, and a slot extending axially from a first end of the first portion to a second end of the first portion;
    a second portion that is generally hollow and cylindrical in shape and includes an axial retaining structure, a pedicle screw retaining structure, and a slot extending axially from a first end of the second portion to a second end of the second portion; and a third portion that is generally hollow and cylindrical in shape and includes an axial retaining structure and a slot extending axially from a first end of the third portion to a second end of the third portion;

wherein the axial retaining structure of the first portion telescopically engages the axial retaining structure of the second portion so as to selectively retain the first portion in a desired axial position relative the second portion; and wherein the axial retaining structure of the second portion telescopically engages the axial retaining structure of the third portion so as to selectively retain the second portion in a desired axial position relative the third portion.

2. The pedicle screw insertion assembly defined in claim 1 wherein the first portion further includes a drive structure that is adapted to be engaged by a tool to effect rotation of the first portion.

3. The pedicle screw insertion assembly defined in claim 1 wherein the axial retaining structure provided on the first portion includes a plurality of annular protrusions and the axial retaining structure provided on the second portion includes a plurality of annular protrusions.

4. The pedicle screw insertion assembly defined in claim 1 wherein the axial retaining structure provided on the second portion includes a plurality of annular protrusions and the axial retaining structure provided on the third portion includes a plurality of annular protrusions.

5. The pedicle screw insertion assembly defined in claim 1 wherein the axial retaining structure provided on the first portion includes a plurality of annular protrusions, the axial retaining structure provided on the second portion includes a plurality of annular protrusions, and the axial retaining structure provided on the third portion includes a plurality of annular protrusions.

6. The pedicle screw insertion assembly defined in claim 1 wherein the first portion has an outwardly extending protrusion that is received within a slot provided on the second portion.

7. The pedicle screw insertion assembly defined in claim 1 wherein the pedicle screw retaining structure of the second portion includes a lip that extends inwardly about the second end thereof.

8. The pedicle screw insertion assembly defined in claim 1 wherein the slots extending through the first portion, the second portion, and the third portion are axially aligned with one another.

9. The pedicle screw insertion assembly defined in claim 1 further including an alignment bracket that is pivotably secured to the first end of the third portion.

10. The pedicle screw insertion assembly defined in claim 9 wherein the first end of the third portion has a pair of arms provided thereon, and wherein the alignment bracket has a pair of arms provided thereon that cooperate with the pair of arms provided on the first end of the third portion to pivotably secure the alignment bracket to the third portion.

11. The pedicle screw insertion assembly defined in claim 1 wherein the first end of the first portion has the axial retaining structure provided thereon, and wherein the second end of the first portion has the pedicle screw drive structure provided thereon.

12. The pedicle screw insertion assembly defined in claim 11 wherein the first end of the second portion has the axial retaining structure provided thereon, and wherein the second end of the second portion has the pedicle screw retaining structure provided thereon.

13. The pedicle screw insertion assembly defined in claim 12 wherein the second end of the third portion has the axial retaining structure provided thereon.

14. The pedicle screw insertion assembly defined in claim 1 wherein the axial retaining structure of the first portion is provided on an outer surface thereof and the axial retaining structure of the second portion is provided on an inner surface thereof.

15. The pedicle screw insertion assembly defined in claim 1 wherein the axial retaining structure of the second portion is provided on an inner surface thereof and the axial retaining structure of the third portion is provided on an outer surface thereof.

16. The pedicle screw insertion assembly defined in claim 1 wherein the axial retaining structure of the first portion is provided on an outer surface thereof, the axial retaining structure of the second portion is provided on an inner surface thereof, and the axial retaining structure of the third portion is provided on an outer surface thereof.

* * * * *